US008181273B2

(12) United States Patent
Kane

(10) Patent No.: US 8,181,273 B2
(45) Date of Patent: May 22, 2012

(54) DISPOSABLE SKIRTS AND SHORTS DIAPERS

(76) Inventor: Michelle Kane, Orange, CA (US)

(*) Notice: Subject to any disclaimer, the term of this patent is extended or adjusted under 35 U.S.C. 154(b) by 157 days.

(21) Appl. No.: 12/359,915

(22) Filed: Jan. 26, 2009

(65) Prior Publication Data

US 2010/0191208 A1  Jul. 29, 2010

(51) Int. Cl.
  A41B 13/08  (2006.01)
  A61F 13/15  (2006.01)
  A61F 13/20  (2006.01)
(52) U.S. Cl. .................. 2/111; 604/385.28
(58) Field of Classification Search ............ 604/385.01, 604/385.21, 385.22, 385.23, 385.24, 385.25, 604/385.29, 385.3; 2/75, 80, 111, 67
See application file for complete search history.

(56) References Cited

U.S. PATENT DOCUMENTS

| 876,173 | A | * | 1/1908 | Guttman | 604/394 |
|---|---|---|---|---|---|
| 1,758,740 | A | * | 5/1930 | Gale | 2/78.2 |
| 2,431,571 | A | * | 11/1947 | Lehr | 2/402 |
| 2,453,051 | A | * | 11/1948 | Vacca | 2/67 |
| 2,483,076 | A | * | 9/1949 | Vacca | 2/67 |
| 2,629,380 | A | * | 2/1953 | Schweikert | 604/399 |
| 3,648,699 | A | * | 3/1972 | Anderson et al. | 604/394 |
| 3,714,946 | A | * | 2/1973 | Rudes | 604/394 |
| 4,028,740 | A | * | 6/1977 | Luerken | 2/67 |
| 4,114,621 | A | * | 9/1978 | Mims, Jr. | 604/361 |
| 4,280,230 | A | * | 7/1981 | LaFleur | 2/408 |
| 4,302,853 | A | * | 12/1981 | Mesek | 2/402 |
| 4,573,987 | A | | 3/1986 | Lamb, Jr. | |
| 4,694,511 | A | * | 9/1987 | Estes et al. | 2/69 |
| 5,444,245 | A | * | 8/1995 | Kitamura | 250/307 |
| 5,876,394 | A | * | 3/1999 | Rosch et al. | 604/393 |
| 5,956,765 | A | * | 9/1999 | Chin | 2/69 |
| 6,009,558 | A | * | 1/2000 | Rosch et al. | 2/212 |
| 6,010,586 | A | * | 1/2000 | Suprise | 156/73.1 |
| 6,035,439 | A | * | 3/2000 | Chin | 2/67 |
| 6,115,847 | A | * | 9/2000 | Rosch et al. | 2/238 |
| 6,217,563 | B1 | | 4/2001 | Van Gompel | |
| 6,293,936 | B1 | * | 9/2001 | Otsubo | 604/396 |
| 6,293,937 | B2 | * | 9/2001 | Matsushita et al. | 604/396 |
| 6,497,694 | B1 | * | 12/2002 | Rosch et al. | 604/385.28 |
| 6,863,665 | B2 | * | 3/2005 | Rosch et al. | 604/385.28 |
| 7,260,852 | B2 | * | 8/2007 | Sheetz | 2/67 |

(Continued)

FOREIGN PATENT DOCUMENTS

EP  1077054  *  2/2001

*Primary Examiner* — Alissa L Hoey
*Assistant Examiner* — Amber Anderson
(74) *Attorney, Agent, or Firm* — Ardent Law Group, P.C.

(57) ABSTRACT

The present embodiment of the subject inventive matter is a one piece disposable diaper clothing that generally comprises of at least one waistband, a diaper that is attached to the at least one waistband and at least one panel that is attached to the at least one waistband. The waistband includes a fastening means that secures the disposable diaper clothing in place on a child. The at least one panel includes a fabric. The diaper coupled with the at least one panel provides a garment like appearance when worn about the lower torso region of the child. As such, the diaper is placed about the lower torso region of the child thereby keeping the panel towards a front waist of the child. The waistband is extended throughout a rear waist towards the front waist of the child. Then the waistband attached with the panel is secured on a waist of the child by the fastening means.

12 Claims, 5 Drawing Sheets

U.S. PATENT DOCUMENTS

| | | | |
|---|---|---|---|
| 7,344,526 B2 * | 3/2008 | Yang et al. | 604/393 |
| 7,491,196 B2 * | 2/2009 | Franke et al. | 604/396 |
| 7,686,796 B2 * | 3/2010 | Kuen et al. | 604/396 |
| 2003/0226197 A1 * | 12/2003 | Cramer | 2/466 |
| 2004/0186452 A1 | 9/2004 | Sandin | |
| 2006/0167432 A1 | 7/2006 | Sigari | |

* cited by examiner

DISPOSABLE SKIRTS AND SHORTS DIAPERS

BACKGROUND OF THE INVENTION (1) Field of the Invention

This invention relates to diapers, and more particularly to disposable diapers.

(2) Description of Related Art

Diapers that absorb urine and other bodily exudates of the infants have been widely used for infant care. The diapers are made of waterproof layers that absorb the moisture to keep the infant's skin dry. The diapers provide great comfort to the infants and more convenience to the caregiver. Various types of diapers are available, for example disposable diapers and reusable diapers like cloth diapers, plastic diapers etc. The reusable diapers need laundering which is generally a tedious process. It is challenging to keep these diapers hygienic before each use, because of the difficulty in cleaning a soiled and moist diaper. Moreover, these reusable diapers are not biodegradable and cause various ecological problems. Such types of disposable diapers are unattractive in appearance. Therefore, there is a demand for a disposable diaper providing a garment like appearance and which is economical.

U.S. Pat. No. 4,573,987 issued to Lamb, Jr on Mar. 4, 1986 provides a multi-layer diaper for use in contact with skin to absorb body wastes. The multi-layer diaper draws the moisture away from the infant's body and it uses a non-allergenic cotton fabric against the baby's skin. Since this diaper wear is reusable, it should be laundered after each use which is inconvenient. Even though the diapers are washed and dried, they are not completely free from microorganisms that cause infection. Moreover, after repeated washing and drying process, the multiple layers tend to bunch up into one section and become uncomfortable to the infant.

U.S. Pat. No. 6,217,563 issued to Van Gompel on Apr. 17, 2001 discloses an integral absorbent article, such as a diaper, having a longitudinal article length and a lateral article width. The article includes an absorbent composite that has a liquid-impermeable back sheet layer, a liquid permeable top sheet layer, and a retention portion sandwiched between the back sheet and top sheet layers. This diaper has a complicate design and is bulky in appearance. As a result, the cost of manufacturing such articles is undesirably high.

U.S. Patent Application 20040186452 to Sandin on Sep. 23, 2004 provides a pant shaped garment having a rear portion, a front portion, a crotch portion, a waist opening with a waist edge and two leg openings bordered by a leg edge. The front portion comprises an elastically extensible material and an elongated elastic element that constricts the rear part of the leg edge, thereby stretching the elastic material along the front part of the leg edge. The elastic material laminate of front and rear portion comprises an elastic plastic film that is arranged between non-woven layers. Prolonged use of these diapers causes marks and irritation to the child's skin that result in rashes. Since the diaper is made of plastic, it cannot be disposed in an eco-friendly method.

In order to avoid the above problems, U.S. Patent Application 20060167432 to Sigari on Jul. 27, 2006 discloses a reusable pants-type diaper which combines an array of absorbent fabrics and polyurethane laminated material to create a new and unique diapering system. This diaper wear consists of a two or more layer waterproof diaper cover, absorbent disposable or non-disposable insert, and optional outer clothing. However, Sigari requires that the front panel be one rectangular piece and that the back panel is also one rectangular piece. In addition, Sigari requires that the front panel is composed of two pieces. All of these limitations are not found by the present embodiment of the subject inventive matter.

BRIEF SUMMARY OF THE INVENTION

While many of the prior art designs provide a disposable diaper, possible clothing is quite limited since it is designed to support the item for which it was specifically designed. Furthermore, most of these traditional diapers are reusable that cannot be disposed eco-friendly and lacks an aesthetic look.

All referenced patents, applications and literatures are incorporated herein by reference to their entirety. Furthermore, where a definition or use of a term in a reference, which is incorporated by reference herein, is inconsistent or contrary to the definition of that term provided herein, the definition of that term provided herein applies and the definition of the term in the reference does not apply. The invention may seek to satisfy one or more of the above-mentioned desire. Although the present embodiment of the subject inventive matter may obviate one or more of the above-mentioned desires, it should be understood that some aspects of the invention might not necessarily obviate them.

In these respects, the disposable diaper according to the present embodiment of the subject inventive matter substantially departs from the conventional concepts and designs of the prior art, and so doing provides a disposable diaper that is not anticipated, rendered obvious, suggested, or even implied by any of the prior art disposable diaper clothing, either alone or in combination thereof.

In view of the foregoing disadvantages inherent in the known types of disposable diapers now present in the prior art, the general purpose of the present embodiment of the subject inventive matter, which will be described subsequently in greater detail, is to provide a disposable diaper with a fabric that provides a garment like appearance when worn about the lower torso region of a child.

Another object of the present embodiment of the subject inventive matter is to provide a one-piece disposable diaper clothing, which can be conformable for various designs like skirt, short, skort, trousers etc;

Another object of the present embodiment of the subject inventive matter is to provide a disposable diaper clothing, which is comprised of a waistband having fastening means that secures the diaper coupled with the panel in place on the child;

Another object of the present embodiment of the subject inventive matter is to provide a disposable diaper clothing, which is comprised of a standard diaper that is coupled with the panel so that the entire product is disposable;

Another object of the present embodiment of the subject inventive matter is to provide a disposable diaper clothing, which is eco-friendly and easy to use;

Another object of the present embodiment of the subject inventive matter is to provide a disposable diaper clothing, which is comprised of a waistband and a panel that are made of non-woven fabric that includes a spun bond made from polypropylene;

To attain this, the present embodiment of the subject inventive matter in one embodiment generally comprises of a disposable diaper clothing for a child having at least one waistband, a diaper that is attached to the at least one waistband and at least one panel that is attached to the at least one waistband. The at least one panel includes a fabric. The at least one waistband includes at least one fastening means that secures the disposable diaper clothing in place on the child.

In typical use, the diaper is placed about the lower torso region of the child thereby keeping at least one panel towards a front waist of the child. The waistband is extended throughout a rear waist towards the front waist of the child. Then securing the waistband attached with the panel on a waist of the child by at least one fastening means.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of the construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting. To accomplish the above and related objects, this invention may be embodied in the form illustrated in the accompanying drawings, attention being called to the fact, however, that the drawings are illustrative only, and that changes may be made in the specific construction illustrated.

BRIEF DESCRIPTION OF THE DRAWING(S)

Various other objects, features and attendant advantages of the present embodiment of the subject inventive matter will become fully appreciated as the same becomes better understood when considered in conjunction with the accompanying drawings, in which like reference characters designate the same or similar parts throughout the several views, and wherein.

DETAILED DESCRIPTION OF THE INVENTION

The invention and its various embodiments can now be better understood by turning to the following detailed description of the preferred embodiments, which are presented as illustrated examples of the invention defined in the claims. It is expressly understood that the invention as defined by the claims may be broader than the illustrated embodiments described below.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claims are set forth below in a certain combination, it must be expressly understood that the invention includes other combinations of fewer, more or different elements, which are disclosed herein even when not initially claimed in such combinations.

Figure 1:
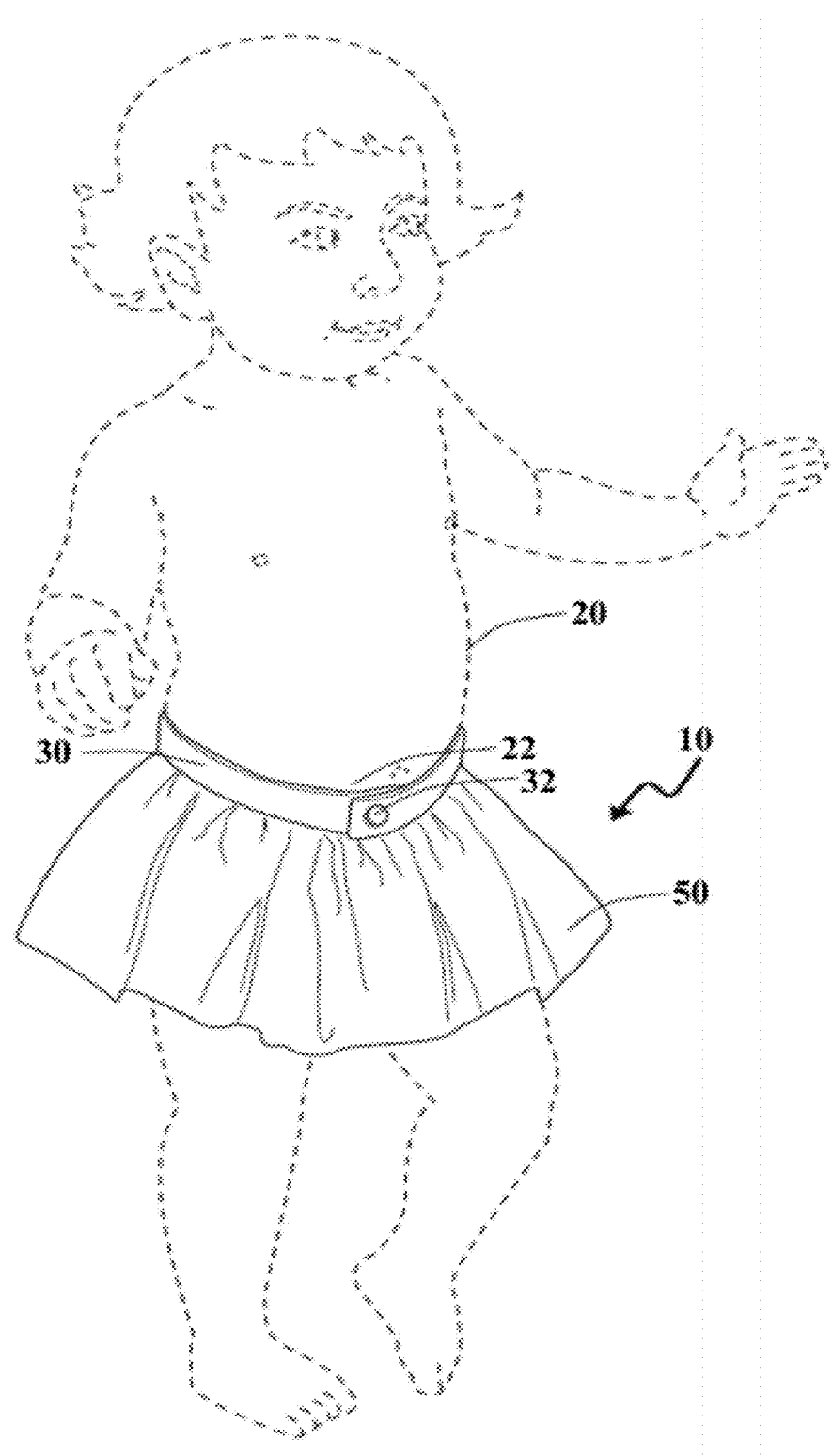
FIG. 1 is a perspective view of a disposable diaper clothing worn by a child in accordance with the present embodiment of the subject inventive matter.

Referring now to the drawings, which are provided by way of illustration and example, and wherein like reference numerals designate like or corresponding elements among the several views, there is shown in FIG. 1, a disposable diaper clothing 10 for a child 20 having at least one waistband 30, a diaper 40 that is attached to the at least one waistband 30 and at least one panel 50 that is attached to the at least one waistband 30. The diaper 40 is coupled with the at least one panel 50 which provides a garment like appearance when worn about a lower torso region (not pictured) of the child 20.

Figure 2:
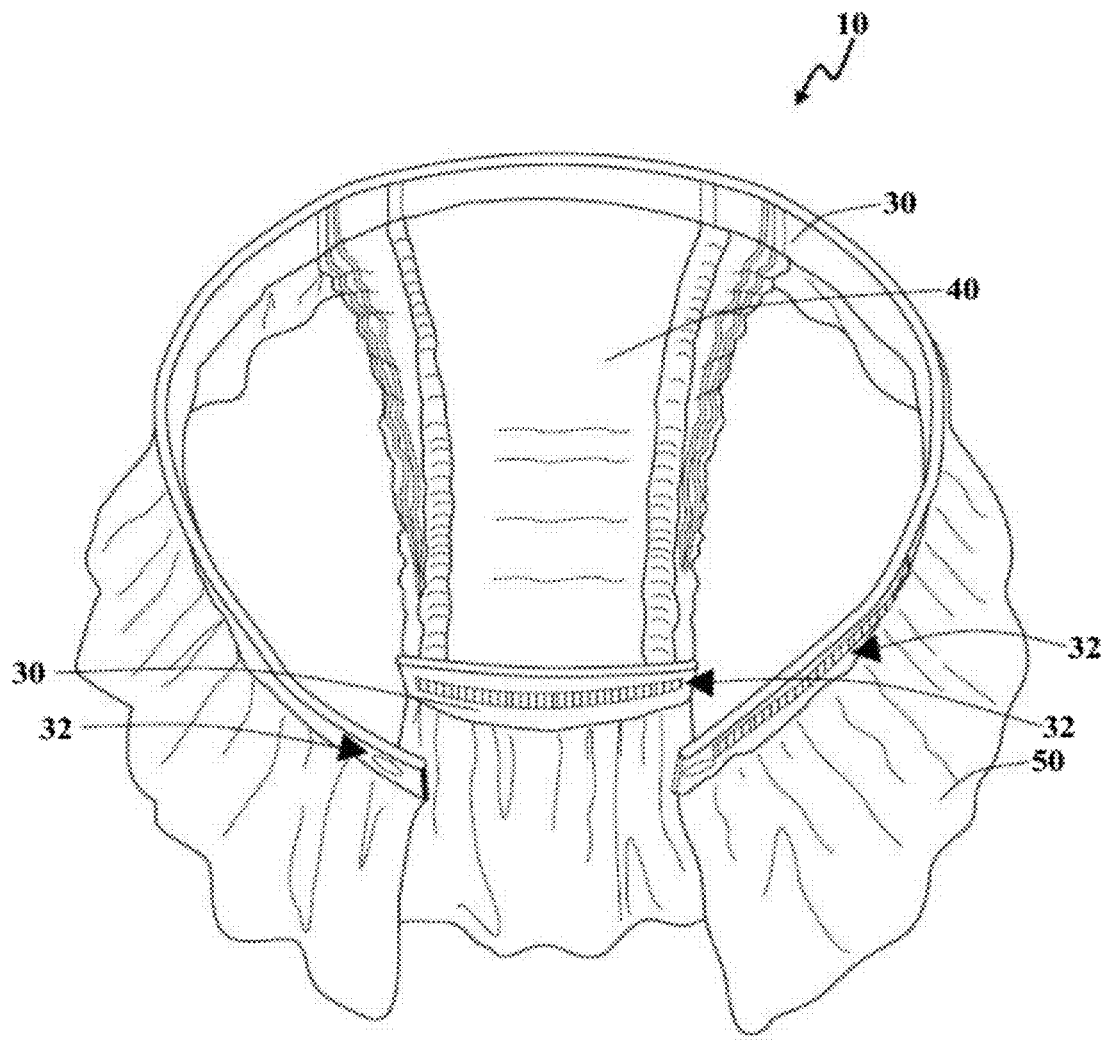
FIG. 2 is a top perspective view of a disposable diaper clothing shown in FIG. 1, illustrating a diaper coupled with at least one panel.

Turning now to the embodiment of FIG. 2, a disposable diaper clothing 10 can be removed from a child's body by detaching at least one fastening means 32 included in at least one waistband 30. A diaper 40 is attached to the at least one waistband 30 by being sewn on. The at least one fastening means 32 is selected from a group consisting of a velcro, snap button, hook and loop fasteners, zipper etc. The at least one fastening means 32 secures the diaper 40 coupled with at least one panel 50 in place on a child 20. The at least one panel 50 includes a fabric. In use, the diaper 40 coupled with the at least one panel 50 provides a garment like appearance. The diaper 40 is placed about the lower torso region (not pictured) of the child 20 thereby keeping the at least one panel 50 towards a front waist (not pictured) of the child 20. The at least one waistband 30 is extended throughout a rear waist (not pictured) towards the front waist (not pictured) of the child 20. Then securing the at least one waistband 30 attached with the at least one panel 50 on a waist 22 of the child 20 by the at least one fastening means 32.

Figure 3:
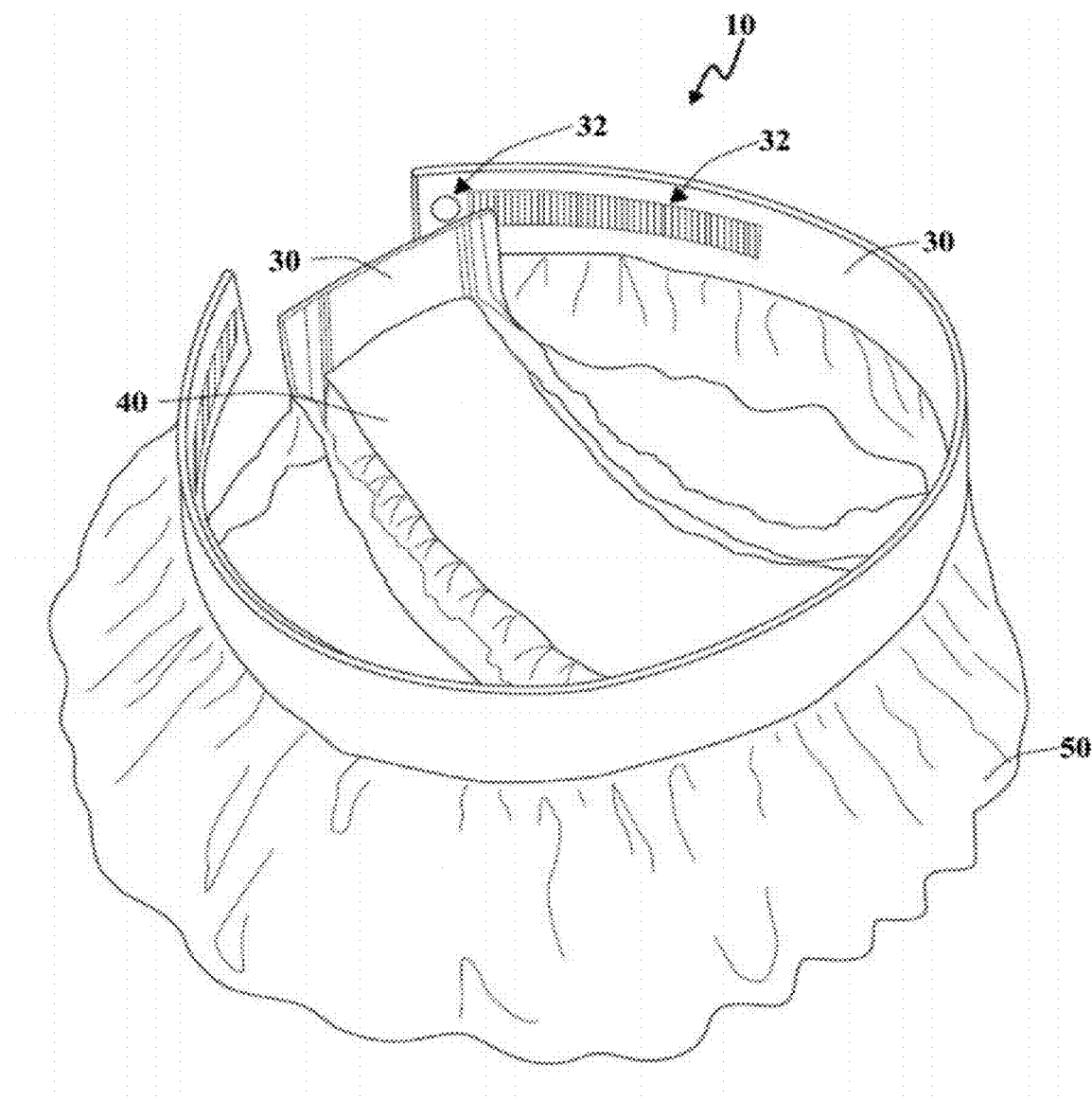
FIG. 3 is a perspective view of an embodiment of the subject matter of the present embodiment of the subject inventive matter.

FIG. 3 shows a top perspective view of a disposable diaper clothing 10. A diaper 40 coupled with at least one panel 50 provides an arrangement selected from a group consisting of a skirt, short, skort, and the like. At least one waistband 30 is made of a non-woven fabric that includes a spun bond made from polypropylene. The at least one panel 50 is made of a non-woven fabric that includes a spun bond made from polypropylene. The spun bond layer is a soft fabric that provides comfort to a child 20 and is absorbent to fluids. This material possesses sufficient strength and extensibility.

Figure 4:
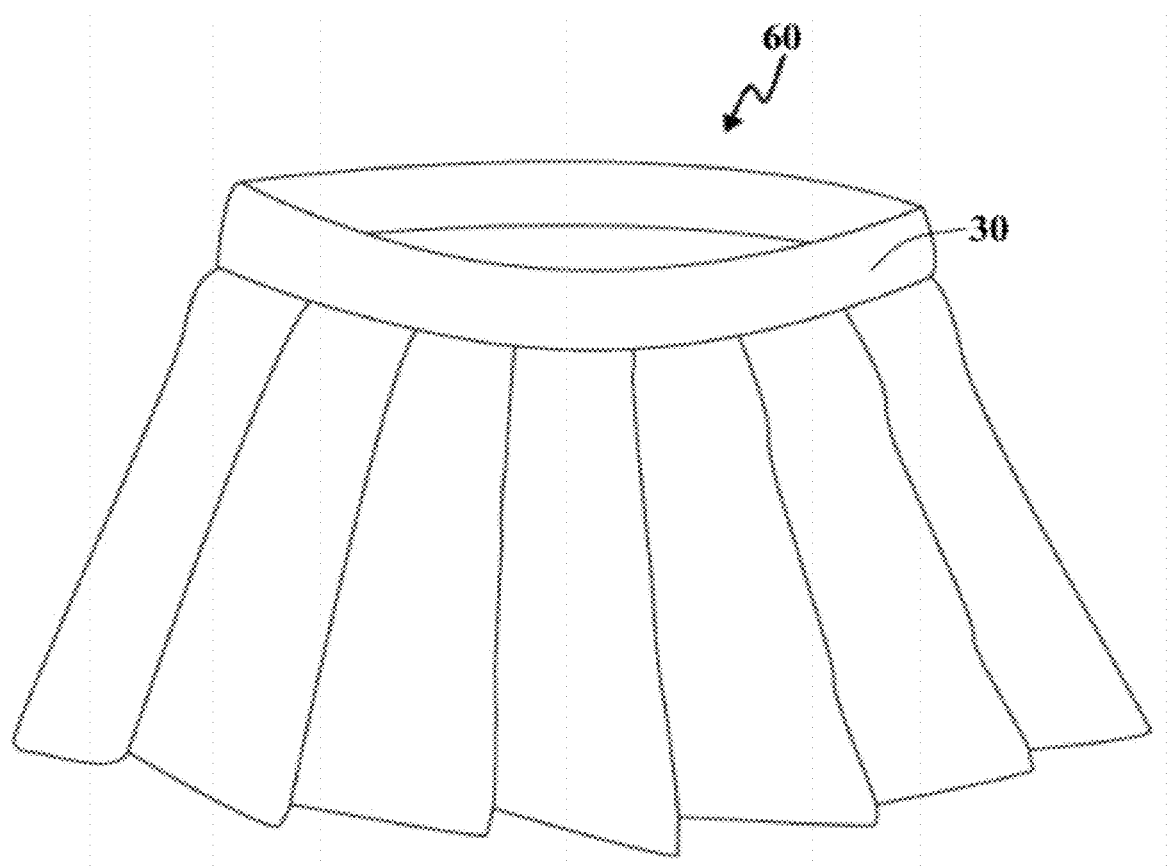
FIG. 4 is a perspective view of an alternate embodiment of the present embodiment of the subject inventive matter.
Figure 5:
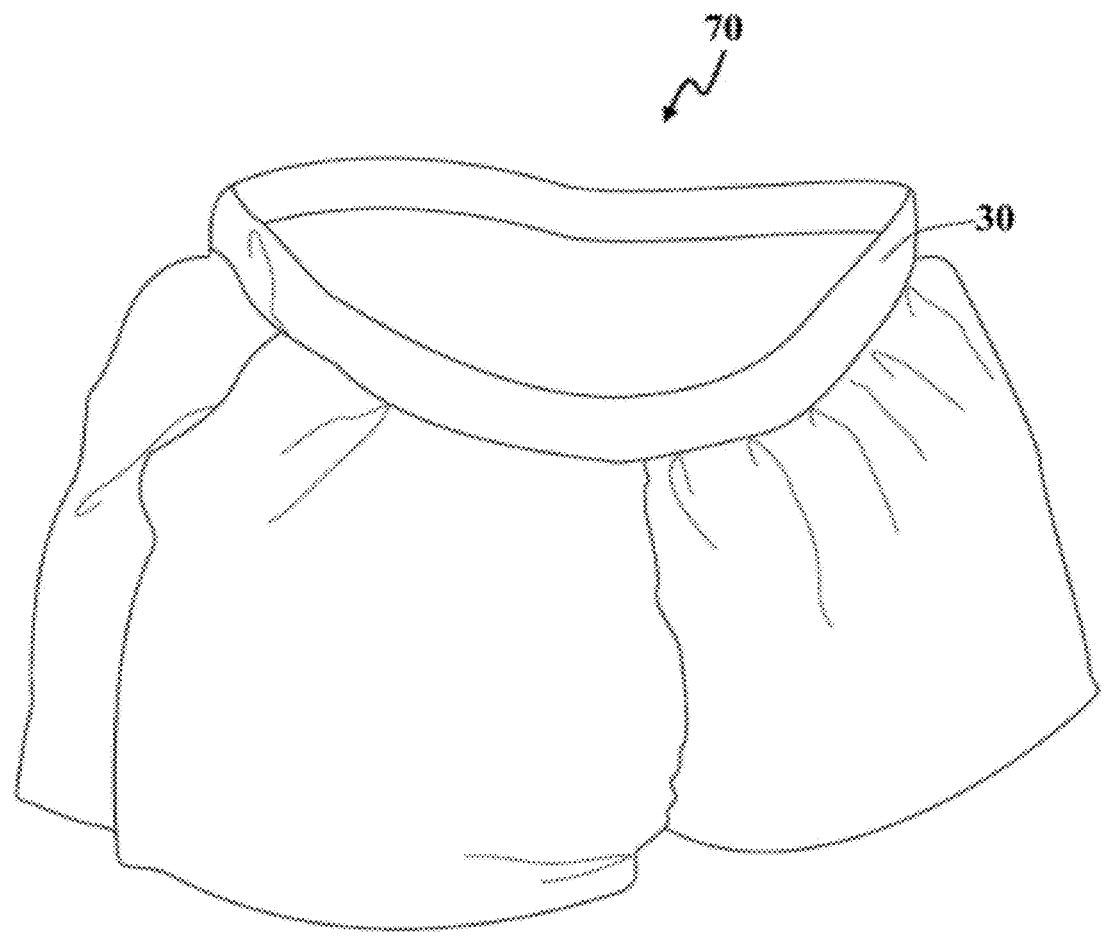
FIG. 5 is a perspective view of an alternate embodiment of the present embodiment of the subject inventive matter.

FIG. 4 and FIG. 5 show a perspective view of alternate embodiments of the invention, illustrating a pleated skirt 60 and a short 70 respectively. At least one panel 50 may be arranged to precisely desired shape to form various designs like pleated skirts, shorts, skorts etc. According to the size of a diaper 40, at least one waistband 30 and the at least one panel 50 may be rendered in one of a plurality of dimensions.

Thus, specific embodiments and applications of the have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A one-piece disposable diaper clothing for a child, comprising:
   at least one waistband;
   a diaper being attached to the at least one waistband; and
   at least one panel being attached to the at least one waistband;
   wherein the at least one panel having a first panel portion and a second panel portion,
   wherein a length of the first panel portion is greater than a length of the second panel portion,
   whereby the diaper is coupled with the at least one panel that provides a garment like appearance when worn about the lower torso region of the child;
   said waistband is coupled by at least one fastening means in a front side of said one-piece disposable diaper clothing for a child,
   wherein the at least one waistband having a first waistband portion and a second waistband portion, wherein the first waistband portion having a first end and a second end, wherein the first end is connected directly to the second end, wherein both the first end and the second end of the first waistband portion is connected to the second waistband portion,
   wherein the length of the first panel portion and a length of the first waistband portion are substantially equal,
   wherein the length of the second panel portion and a length of the second waistband portion are substantially equal,
   wherein an upper end of the first panel portion is attached to a lowermost edge of the first waistband portion and a lower end of the first panel portion is free from attachment,
   wherein an upper end of the second panel portion is attached to a lowermost edge of the second waistband portion and a lower end of the second panel portion is free from attachment,
   wherein when the first end and the second end of the first waistband portion are fastened to each other, the second waistband portion is substantially covered by the first waistband portion,
   wherein when the first end and the second end of the first waistband portion are fastened to each other, the second panel portion is substantially covered by the first panel portion,
   wherein the length of the first panel portion is parallel to a longitudinal axis of the first waistband portion,
   wherein the length of the second panel portion is parallel to a longitudinal axis of the second waistband portion,
   wherein the length of the second waistband portion is less than half the length of the first waistband portion.

2. The disposable diaper clothing as recited in claim 1, wherein the diaper attached to the at least one waistband by being sewn on.

3. The disposable diaper clothing as recited in claim 1, wherein the at least one panel includes a fabric.

4. The disposable diaper clothing as recited in claim 1, wherein the at least one fastening means is selected from a group consisting of a hook and loop fastener, snap button, and zipper.

5. The disposable diaper clothing as recited in claim 1, wherein the diaper coupled with the at least one panel provide an arrangement of a skirt.

6. The disposable diaper clothing as recited in claim 1, wherein the at least one fastening means secures the diaper coupled with the at least one panel in place on the child.

7. The disposable diaper clothing as recited in claim 1, wherein the at least one waistband is made of a non-woven fabric.

8. The disposable diaper clothing as recited in claim 7, wherein the non-woven fabric includes a spun bond made from polypropylene.

9. The disposable diaper clothing as recited in claim 1, wherein the at least one panel is made of a non-woven fabric.

10. The disposable diaper clothing as recited in claim 9, wherein the non-woven fabric includes a spun bond made from polypropylene.

11. The disposable diaper clothing as recited in claim 1, wherein the diaper is connected to the second waistband portion and the second panel portion is only connected to the second waistband portion and separated from the diaper.

12. The disposable diaper clothing as recited in claim 1, wherein the first panel portion has no fastening means.

* * * * *